United States Patent [19]
Tien

[11] Patent Number: 5,588,427
[45] Date of Patent: Dec. 31, 1996

[54] ENHANCEMENT OF PHYSIOLOGICAL SIGNALS USING FRACTAL ANALYSIS

[75] Inventor: Jonathan Tien, Redmond, Wash.

[73] Assignee: SpaceLabs Medical, Inc., Redmond, Wash.

[21] Appl. No.: 559,846

[22] Filed: Nov. 20, 1995

[51] Int. Cl.⁶ .................................................. A61B 5/00
[52] U.S. Cl. ........................................ 128/633; 356/41
[58] Field of Search ............................. 128/633, 664–7; 356/39–41; 364/413.03

[56] References Cited

U.S. PATENT DOCUMENTS

| | | | |
|---|---|---|---|
| 5,040,539 | 8/1991 | Schmitt et al. | 128/633 |
| 5,277,181 | 1/1994 | Mendelson et al. | 128/633 |
| 5,482,036 | 1/1996 | Diab et al. | 128/633 |

Primary Examiner—Angela D. Sykes
Assistant Examiner—Bryan K. Yarnell
Attorney, Agent, or Firm—Seed and Berry LLP

[57] ABSTRACT

A technique for the derivation of a pulse oximetry signal using fractal dimension analysis of detected light signals. First and second light sources transmit light through the patient's finger or reflect light off the blood vessels in the patient's finger. A light detector detects light from each of the light sources and generates a measured intensity signal. The measured intensity signal includes the true intensity of light transmitted from each of the light sources as well as noise introduced during the measurement process. A data sample from each of the light sources is digitized and a set of equations developed as a function of a ratio value indicative of oxygen saturation in the patient. The fractal dimension is determined for the set of signal functions over the normal physiological range for the ratio value. Maximum and/or minimum fractal dimension values are calculated to determine the desired ratio values which are possible indicatives of the ratio of true physiological signals or noise signals. The ratio values are subsequently processed to determine the oxygen saturation within the patient.

30 Claims, 8 Drawing Sheets

ENHANCEMENT OF PHYSIOLOGICAL SIGNALS USING FRACTAL ANALYSIS

TECHNICAL FIELD

The present invention relates generally to signal processing and, more particularly, to a system and method for processing physiological signals in the presence of noise to derive the physiological signals.

BACKGROUND OF THE INVENTION

The measurement of physiological signals is difficult because the underlying physiological processes generate very low level signals and interfering noise is inherent in the body and the interface between the body and sensors of the physiological processes. For example, the measurement of electrocardiogram (ECG) signals is based on the electrical activity generated by the electrical depolarization of the heart muscle. The signals are typically detected by surface electrodes mounted on the chest of the patient. The signals are initially weak at the signal source (i.e., the heart) and are even weaker at the surface of the chest. Furthermore, electrical interference from the activity of other muscles, noise caused by patient breathing, general movement, and the like cause additional interference with the ECG signal. External electrical interference, such as 60 Hertz (Hz) interference, also compounds the ECG measurement problem. Therefore, great care must be taken in the design and use of physiological processors to enhance the quality of the desired signal and reduce the effects of interfering signals.

Another common physiological measurement that is made difficult by the presence of interfering noise is the measure of oxygen saturation in the blood. This measurement is frequently performed with a pulse oximeter 1, illustrated in the functional block diagram of FIG. 1. A transmissive pulse oximetry sensor 2 is placed on a finger 4 of the patient. First and second light sources 6 and 8 are directed through the fleshy portion of the finger 4 and detected by one or more light detectors 10 on the opposite side of the finger. As is well known in the art, the light from light sources 6 and 8 are of different wavelengths that are differentially absorbed by oxygenated blood cells. The first light source 6 is typically designated as a Red light source having a wavelength in the red region of the spectrum. The second light source 8 is typically designated the IR source having a wavelength in the near infrared region of the spectrum.

The pulse oximeter 1 determines the oxygen saturation based on a ratio of the light detected from the Red light source 6 and the IR light source 8, respectively. A ratio calculator 12 determines the ratio of detected light and uses the value of the ratio as an index to a look-up table 14. The look-up table 14 contains data relating the ratio of detected light to the oxygen saturation in the blood. A typical oxygen saturation curve 18 is illustrated in FIG. 2 where the percentage of oxygen saturation is plotted against the ratio of detected light from the Red light source 6 and the IR light source 8 (see FIG. 1). Pulse oximeters may also use reflective pulse oximetry sensors (not shown) in which the light sources and light detectors are positioned adjacent each other, and the light from the light sources is reflected back to the detector(s) by oxygenated blood cells in the finger 4.

The measurement of blood oxygen saturation is important for physicians who are monitoring a patient during surgery and at other times. As with other physiological measurements, pulse oximetry measurement also is susceptible to interference from noise. As is known in the art, pulse oximetry is particularly susceptible to interference from stray light and from patient motion. Stray light detected by the light detector 10 can cause erroneous calculation of the ratio. Known techniques are employed to reduce the interference caused by stray light. The interference from patient motion is a much more difficult noise source and is the subject of intensive research.

Therefore, it can be appreciated that there is a significant need for a system and method for measurement of physiological signals that enhances the desired signal in the presence of interfering noise signals. This and other advantages provided by the present invention are described in the detailed description and accompanying figures.

SUMMARY OF THE INVENTION

The present invention is embodied in a system and method for the enhancement of physiological signals. The system comprises a sensor positioned in proximity with the subject to detect physiological signals and to generate signals indicative of the detected physiological signals. Each of the detected signals has a first portion arising from the physiological phenomenon and a second portion arising from an interference source. A signal processor, responsive to a control signal, processes the detected signals and generates processed signals. An analyzer analyzes and determines the complexity value for the processed signals, with the analyzer selecting a value for the control signal that results in a selected value for said complexity value.

The analyzer may be a fractal analyzer that determines a fractal value for the complexity value. In one embodiment, the analyzer selects a value for the control signal that results in a maximum value for the complexity value. In another embodiment, the analyzer selects a value for the control signal that results in a minimum value for the complexity value. In yet another embodiment, the control signal is valid over a predetermined range, and the analyzer selects a value for the control signal in that predetermined range.

The signal processor in the system may be an adaptive signal processor with a signal input, a reference input, and adaptive filter coupled to the reference input and generating the filter output and a summer coupled to the signal input and the filter output to generate a summer output. The signal input receives the detected signals and the reference input receives a signal derived from a mathematical relationship of the first and second portions of the detected signals. The analyzer analyzes the processed output to determine the complexity value.

In another embodiment, the system is used to detect pulse oximetry signals from a patient and includes first and second light signals transmitted from first and second light sources having first and second wavelengths, respectively. Each of the detected signals has first and second portions. The system further includes a light detector position to detect the first and second light signals after interacting with the subject and to generate signals indicative of an intensity of the first and second detected light signals. A storage location contains a mathematical relationship of the first and second portions of the first and second detected signals and a first ratio of the first portion of the first detected signal to the first portion of the second detected signal. The analyzer is coupled to the storage location and determines a plurality of complexity values for the mathematical relationship over a predetermined range of the first ratio, with the first ratio being based on the complexity values. In one embodiment, the first ratio has a selected value that is determined by finding a maximum value for the plurality of complexity values. In one embodiment, the first ratio is indicative of blood oxygen saturation in the subject, and the system further includes a look-up table containing data relating the first ratio to the blood oxygen saturation levels.

DETAILED DESCRIPTION OF THE INVENTION

Figure 1:
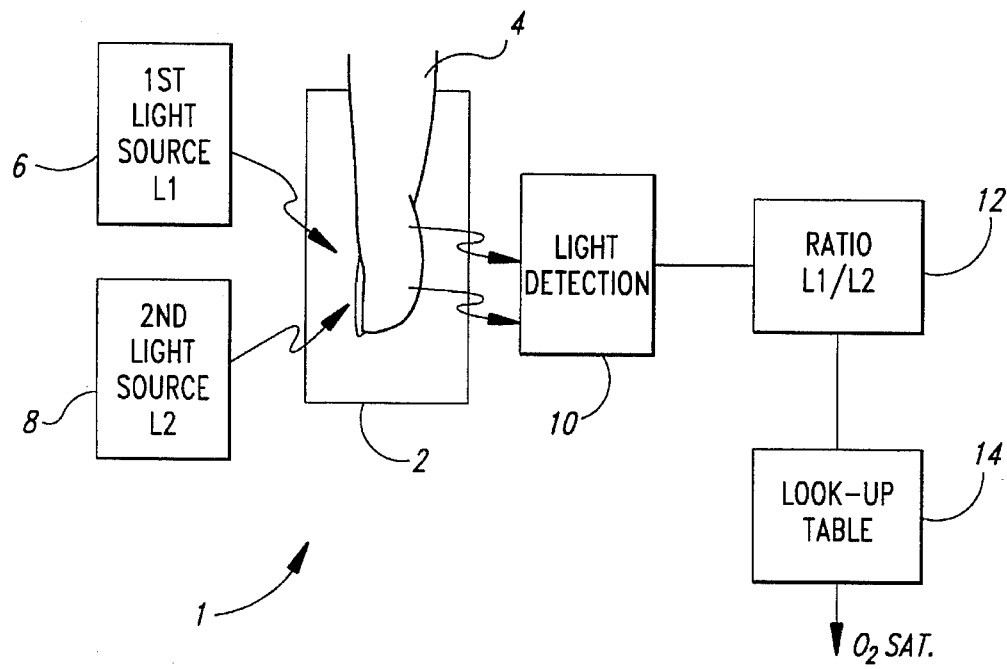
FIG. 1 is a functional block diagram of a prior art oximetry system.

Measurement of physiological signals in the presence of interference is a difficult task, particularly if the interference is somewhat random rather than periodic. A number of different techniques can potentially be used to separate the desired physiological signal from the interfering noise signal. For example, a filter can sometimes be used to remove the interfering noise signal. Notch filters, such as a 60 Hz notch filter, can be used to minimize interference from line noise. Similarly, high frequency interference noise signals can be eliminated with a lowpass filter designed to pass the physiological signal of interest and to reject frequencies above the physiological signal bandwidth. However, some interference sources have the same or similar frequency content as the physiological signal of interest. For interference of this type, different signal processing technologies must be employed.

Adaptive signal processing is one well-known technique for the separation of a desired signal from an interference signal. Adaptive signal processing is based on the assumption that the noise caused by the interference signal is uncorrelated to the desired signal. A conventional adaptive signal processor, configured as a correlation canceller, is illustrated in the functional block diagram of FIG. 3. An adaptive processor 15 has a signal input 16 and a noise reference input 17. The noise reference input 17 is fed to an adaptive filter 18. The adaptive filter 18 generates a filter output 19 that is subtracted from the signal input 16 in a conventional subtractor 20. The subtractor 20 generates an error signal 21, having a value designated herein as a, that is fed back to the adaptive filter 18. The adaptive filter 18 is automatically adjusted so that the error signal 21 has a minimum correlation with the noise reference input 17. Thus, the adaptive filter 18 is adjusted so that the subtractor 20 cancels any correlated signal in the signal input 16. The error signal 21 is the system output and contains the portion of the input signal 16 that is uncorrelated to the noise reference input 17. In a typical application of adaptive filtering, the signal input 16 consists of a combination of a pure input signal from a device, such as a sensor, and a noise signal from one or more sources. The noise reference input 17 should then be a signal that is related to, and at least partially correlated with, the noise signal. Furthermore, the noise reference input should not contain a desired signal. The adaptive filter 18 is adjusted so that the error signal 21 is the pure input signal since the pure input signal has a minimum correlation with the noise reference signal applied to the noise reference input 17.

Adaptive signal processing has been successfully applied to the measurement of physiological signals when the source of the interference signal is well characterized. For example, the physician may wish to listen to a fetal heartbeat whose acoustical signal strength is relatively small compared to the acoustical strength of the mother's heartbeat. As discussed above, simple filtering will not work satisfactorily because the two heartbeats have similar frequency content. However, adaptive signal processing can isolate the fetal heartbeat by using the much louder maternal heartbeat as the noise reference input 17 and the combination of fetal and maternal heartbeats as the signal input 16. Because the two heartbeats are uncorrelated and the maternal heartbeat can be independently derived, the adaptive signal processor 15 can easily isolate the fetal heartbeat. Similarly, the adaptive signal processor 16 can remove 60 Hz interference by simply using the 60 Hz signal as the noise reference input 16. Thus, adaptive signal processing can effectively remove the undesirable interference signal provided that the interference signal can be independently derived.

However, some physiological signals of interest do not have an independent interference source to use as the noise reference input 17. For example, pulse oximetry is susceptible to motion artifact, as described above. The motion alters the path that the light takes through the finger 4 (see FIG. 1) and the characteristics of the interface between the finger 4 and the sensor 2. As the light from the Red light source 6 and the IR light source 8 pass through the fleshy portion of the finger 4, each is contaminated by a noise signal, primarily due to patient motion. The detected light is thus the combination of the true light transmitted through the finger 4 plus the interfering noise introduced in the measurement process. This may be illustrated by the following equations:

$$R = R^* + N \tag{1}$$

$$r = r^* + n \quad (2)$$

where R is the light intensity measured by the light detector 10 (see FIG. 1), R* is the true intensity of light transmitted by the Red light source 6, and N is the noise source introduced by the measurement process while measuring the intensity of the Red light. Similarly, r in equation (2) is the light intensity measured by the light detector 10, r* is the true intensity of light transmitted by the IR light source 8, and n is the noise source introduced by the measurement process while measuring the intensity of the IR light.

The goal of the measurement process is to determine the ratio of the true intensity of Red light, R* transmitted through the finger 4 to true intensity of IR light, r* transmitted through the finger. However, most pulse oximetry systems determine the ratio of the measured signals (i.e., R/r) or some processed version of the measured intensities due to an inability to determine the true intensity.

Some prior art pulse oximetry systems attempt to minimize the effects of motion artifact through conventional filtering or modulation of the intensity of the light sources 6 and 8. However, these processing techniques are not particularly effective because the motion artifact is caused primarily by movement of venous blood in the tissues of the finger 4 rather than from some external noise source such as stray light. Conventional filtering may remove some undesirable noise, but the frequency content of the motion artifact is similar to that of the desired signal. Modulation techniques may reduce interference from stray ambient light, but have little effect on motion artifact because the primary noise source (e.g., venous blood movement resulting from patient motion) originates in the measurement pathway. Thus, the ratio determined by many pulse oximetry systems is not accurate.

It should be noted that the intensity of detected light varies with the patient's heartbeat thus creating a time-varying pulsatile waveform. The pulsatile waveform contains an alternating current (AC) signal component and a direct current (DC) component. In practice, it is generally simple to compensate for the effects of the DC components. Thus, equations (1) and (2) above may be more accurately shown as:

$$R(t) = R^*(t) + N(t) \quad (3)$$

$$r(t) = r^*(t) + n(t) \quad (4)$$

to reflect the time varying nature of the signals.

Figure 5:
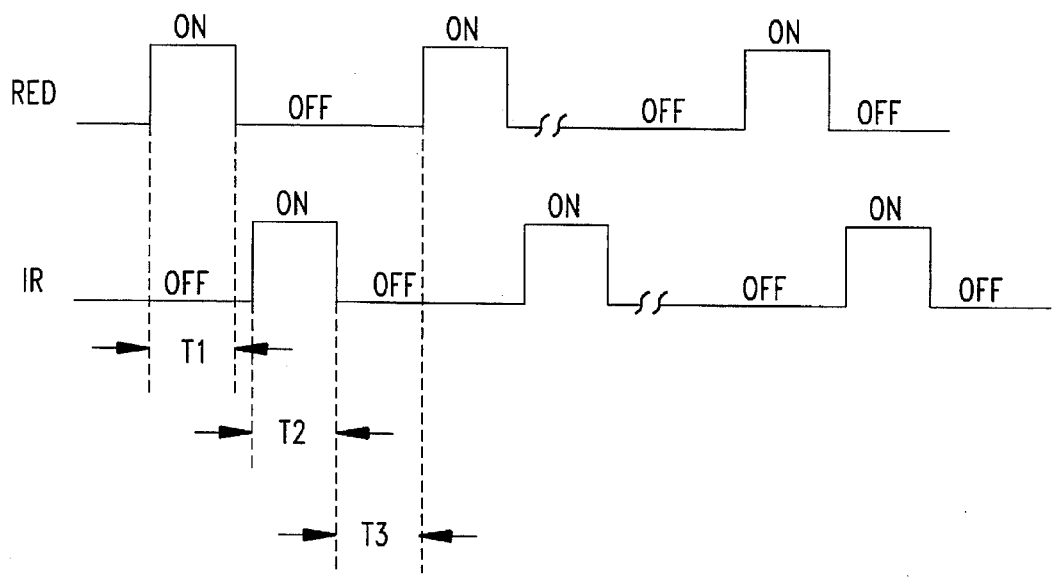
FIG. 5 are waveforms that illustrate the timing control of light sources used by the system of FIG. 4.
Figure 4:
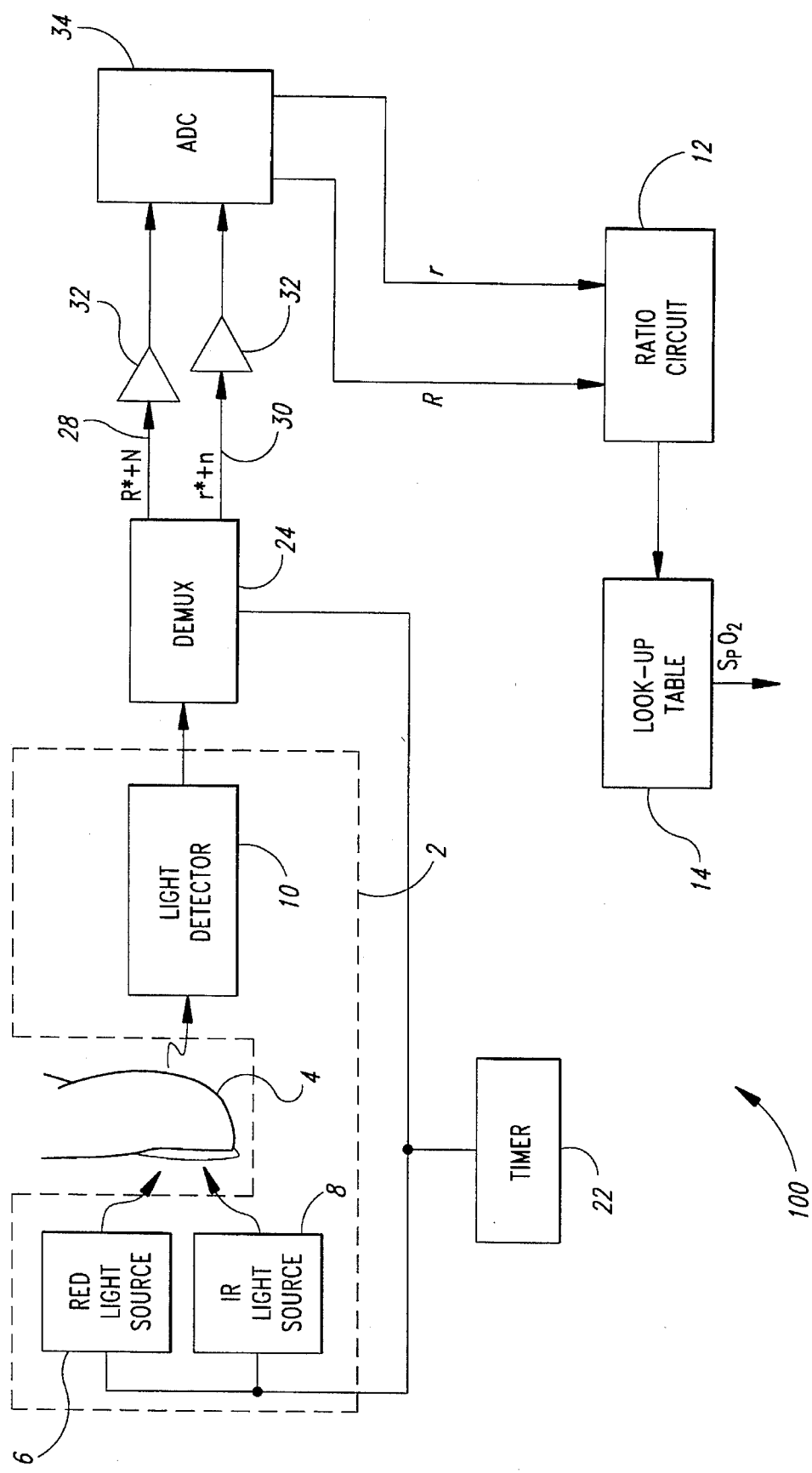
FIG. 4 is a detailed functional block diagram of the system of FIG. 1.

The typical prior art transmissive pulse oximetry system 1, illustrated in FIG. 1, is shown in greater detail in the functional block diagram of FIG. 4, where the sensor 2 contains the Red light source 6 and the IR light source 8, typically on the same side of the patient's finger 4. The Red and IR light sources 6 and 8 are alternately activated by a timer 22. The activation timing of the first and second light sources 6 and 8 is illustrated in the waveform of FIG. 5. The Red light source 6 is activated in the period T1. Following the period T1, the IR light source 8 is activated during the period T2. Following the period T2, neither the Red light source 6 or the IR light source 8 is activated during the period T3. The pulse oximeter uses the period T3 to detect stray ambient light and determine a baseline value to compensate for the stray ambient light. Compensation of stray light is well known by those of ordinary skill in the art and will not be discussed herein.

Returning again to FIG. 4, the timer 22 repeats the pulsation of the Red light source 6 and the IR light source 8 in the manner described above. It should be noted that the intensity of the light from the Red light source 6 and the IR light source 8 is automatically adjusted by a closed-loop system to assure an acceptable detected signal level. This closed-loop gain control is well known in the art and need not be discussed herein.

The detector 10 detects light transmitted through the fleshy portion of the finger 4. The signals generated by the light detector 10 are passed to a demultiplexer 24. The demultiplexer 24 is coupled to the timer 22 and is controlled by the timer to generate an independent signal for the light detected from each of the light sources 6 and 8, respectively. The time division multiplexing used by the system 1 is well understood and will not be discussed in detail herein. As discussed above, the timer 22 enables the Red light source 6 during the period T1 (see FIG. 5). During that same period T1, the timer 22 also controls the demultiplexer 24 so that the detected signals from the Red light source 6 are routed to a data line 28. During the time period T2, the timer 22 enables the IR light source 8 and controls the demultiplexer 24 so that the detected signals from the IR light source are routed to a data line 30. Each of the data lines 28 and 30 can be coupled to optional amplifiers 32. The amplified signals are coupled to the inputs of an analog to digital converter (ADC) 34 that digitizes the signal in a conventional manner. It should be noted that the amplifiers 32 may be integrally formed as part of the ADC 24. The ADC 34 may also include optional lowpass filters (not shown) to assure that the analog signals are bandlimited below the Nyquist rate of the ADC.

The demultiplexer 24 is shown as a separate component in FIG. 4 for the sake of clarity. Those skilled in the art will recognize that the demultiplexing function can also occur after the signal from the light detector 10 has been digitized. The present invention is intended to encompass all such conventional techniques for demultiplexing the signals from the light detector 10.

The ratio circuit 12 receives the digitized signals and uses the ratio of R(t)/r(t) to determine a location in the look-up table 14. Assuming that no motion artifact is present, the data entry in the look-up table 14 corresponds to the blood oxygen saturation. In reality, the ratio calculated by the ratio circuit 12 may be inaccurate because of the motion artifact.

Figure 6:
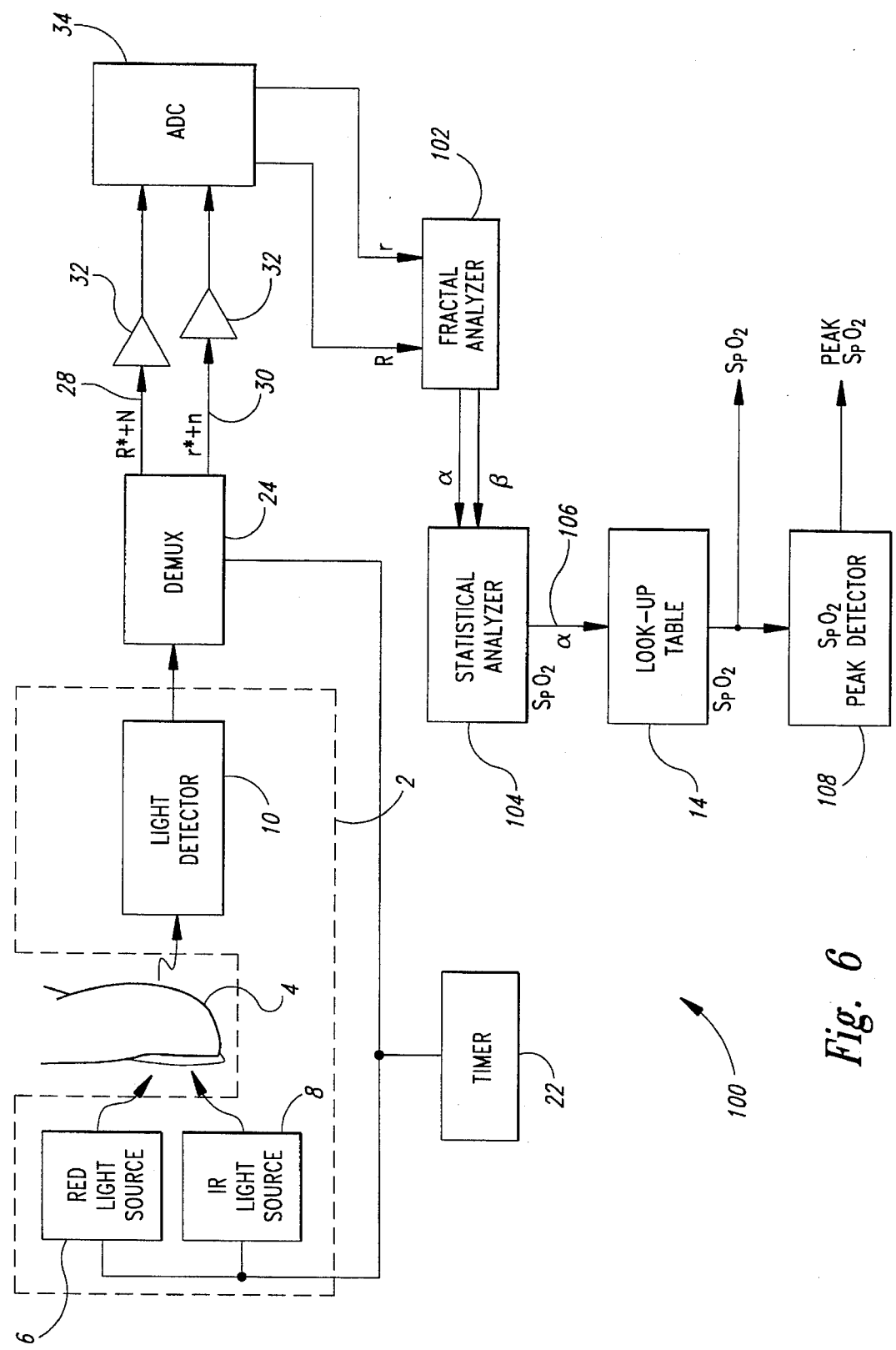
FIG. 6 is a functional block diagram of the present invention used with the system of FIG. 4.

The present invention uses fractal dimension analysis to determine the complexity of waveforms and to determine the proper value of the ratio of true intensities based on signal complexity. The present invention is embodied in a system 100, illustrated in the functional block diagram of FIG. 6. Many components of the system 100 are conventional components used in prior art systems. For example, the sensor 2, demultiplexer 24, and ADC 34 operate in the same manner as do pulse oximetry systems of the prior art. However, the ratio circuit 12 of the prior art is replaced by a fractal analyzer 102. Operational details of the fractal analyzer 102 are provided below. The fractal analyzer 102 determines the proper value for the ratio of the true intensities and thus provides a more accurate calculation for the oxygen saturation.

For purposes of the following description, the ratio of the true intensities may be defined by the following equation:

$$\alpha = \frac{R^*(t)}{r^*(t)} \quad (5)$$

where R*(t) is the time varying true intensity of light transmitted from the Red light source 6 and r*(t) is the time varying true intensity of light transmitted from the IR light source 8. The ratio of noise signals introduced by the measurement process is defined by the equation:

$$\beta = \frac{N(t)}{n(t)} \qquad (6)$$

where N(t) is the noise introduced during the measurement of the light transmitted by the Red light source 6 and n(t) is the noise introduced during the measurement of the light transmitted by the IR light source 8. The fractal analyzer determines values for $\alpha$ and $\beta$ and provides the ($\alpha,\beta$) pairs to a statistical analyzer 104. The statistical analyzer 104 performs additional statistical analysis of one or more ($\alpha,\beta$) pairs to determine the best value for $\alpha$. The best value for $\alpha$ is provided to the look-up table 14 using a data line 106.

The output of the lookup table 14 is a value $S_PO_2$ corresponding to the arterial oxygen saturation in the patient. The system 100 may also include an optional $S_PO_2$ peak detector 108 to generate signals indicative of the peak oxygen saturation. Once the best value for $\alpha$ has been determined, the system 100 can produce pulsatile waveforms of the true intensities R*(t) and r*(t) using the mathematical relations described below. The true intensity pulsatile waveforms are useful for monitoring the patient oximetry waveforms and for calculating continuous blood pressure measurements. Techniques for calculating blood pressure from pulse oximetry output waveforms are described in U.S. Pat. No. 5,269,310. The system 100 can be readily implemented on a conventional digital computer (not shown).

The limitation in the range of values for $\alpha$ and $\beta$ is imposed by the physiology. That is, the oxygen saturation value lies between 100% and 0%, corresponding to a value for the ratio $\alpha$ between 0.3 to 3.0. It is also known that the following constraint exists between $\alpha$ and $\beta$: $\alpha<\beta$ because of the physiological nature of the signals. These conditions can be expressed as:

$$0.3 \left( \frac{r_{DC}}{R_{DC}} \right) < \alpha < \beta < 3.0 \left( \frac{r_{DC}}{R_{DC}} \right) \qquad (7)$$

In equation (7), $r_{DC}$ is a DC component of the light intensity r measured by the light detector 10 from the IR light source 8 and $R_{DC}$ is a DC component of the light intensity R measured by the light detector 10 from the Red light source 6. The ratio of DC components is one technique to compensate for the effects of the DC components of the measured signals and gives a normalized result.

It is noted that the percentage of oxygen saturation is also a time-varying signal, but it changes very slowly over time (approximately 0.5% over 5 seconds). However, it is assumed that the blood oxygen saturation is constant over the short period (e.g., 5 seconds of time) required to perform the calculation. Thus, $\alpha$ and $\beta$ can be considered ratio constants for purposes of the present discussion.

The four equations (3)–(6) can be combined using the following matrix equation:

$$\begin{bmatrix} 1 & 0 & 1 & 0 \\ 0 & 1 & 0 & 1 \\ 1 & -\alpha & 0 & 0 \\ 0 & 0 & 1 & -\beta \end{bmatrix} \times \begin{bmatrix} R^*(t) \\ r^*(t) \\ N(t) \\ n(t) \end{bmatrix} = \begin{bmatrix} R(t) \\ r(t) \\ 0 \\ 0 \end{bmatrix} \qquad (8)$$

where it is assumed that $\alpha \neq \beta$. As previously stated, it is known that the primary cause of noise in transmissive pulse oximetry measurements is motion artifact caused by the movement of venous blood in the finger 4. Thus, the value $\beta$ in equation (6) is related to oxygen saturation in the venous blood. The assumption that $\alpha \neq \beta$ is based on the understanding that $\alpha$ is a measure of arterial blood oxygenation while $\beta$ is related to venous blood oxygenation. As the body takes oxygen from the blood, blood oxygenation decreases as blood moves from the arterial portion of the circulation system to the venous portion of the circulation system. Thus, the measure of arterial oxygenation, measured by $\alpha$, is not the same as $\beta$, which is related to venous oxygenation.

The significance of equation (8) is that all signal components can be explicitly calculated as a function of the input signals and the ratio constants $\alpha$ and $\beta$. The true signal components, R*(t) and r*(t), can also be explicitly derived using equation (8) above. The true signal components, R*(t) and r*(t), can be expressed in terms of the measured signals, R(t) and r(t), by the following equations, which are derived from equation (8):

$$R^*(t) = \frac{\alpha R(t) - \alpha \beta r(t)}{\alpha - \beta} \qquad (9)$$

$$r^*(t) = \frac{R(t) - \beta r(t)}{\alpha - \beta} \qquad (10)$$

Similarly, the noise signals, N(t) and n(t), can be expressed in terms of the measured signals, R(t) and r(t), by the following equations, which are also derived from equation (8):

$$N(t) = \frac{\alpha \beta r(t) - \beta R(t)}{\alpha - \beta} \qquad (11)$$

$$n(t) = \frac{\alpha r(t) - R(t)}{\alpha - \beta} \qquad (12)$$

It will be noted that the above equations (9)–(12) provide the true signal components, R*(t) and r*(t), and the noise components, N(t) and n(t), as a function of the measured signals, R(t) and r(t), available from the sensor 2 (see FIG. 4) and the ratio constants $\alpha$ and $\beta$. The values of the ratio constants $\alpha$ and $\beta$ are not known and must be determined.

It can be shown that the ratio constants $\alpha$ and $\beta$ are interrelated. If one assumes that the true signal and the noise signal are uncorrelated, the signals r*(t) and n(t) are said to be "orthogonal." This may be defined mathematically by the following equation:

$$\int_t r^*(t) n(t) = 0 \qquad (13)$$

which may also be expressed as:

$$\int_t \frac{(\alpha r(t) - R(t))(R(t) - \beta r(t))}{(\alpha - \beta)^2} = 0 \qquad (14)$$

by conventional mathematical manipulation of equations (8)–(13).

Using the previous assumption that $\alpha \neq \beta$, the following equations relate the ratio constants $\alpha$ and $\beta$:

$$\alpha = \frac{\int_t R^2(t) - \beta \int_t R(t) r(t)}{\int_t R(t) r(t) - \beta \int_t r^2(t)} \qquad (15)$$

$$\beta = \frac{\int_t R^2(t) - \alpha \int_t R(t) r(t)}{\int_t R(t) r(t) - \alpha \int_t r^2(t)} \qquad (16)$$

which solve equation (14) for $\alpha$ and $\beta$, respectively.

Figure 2:
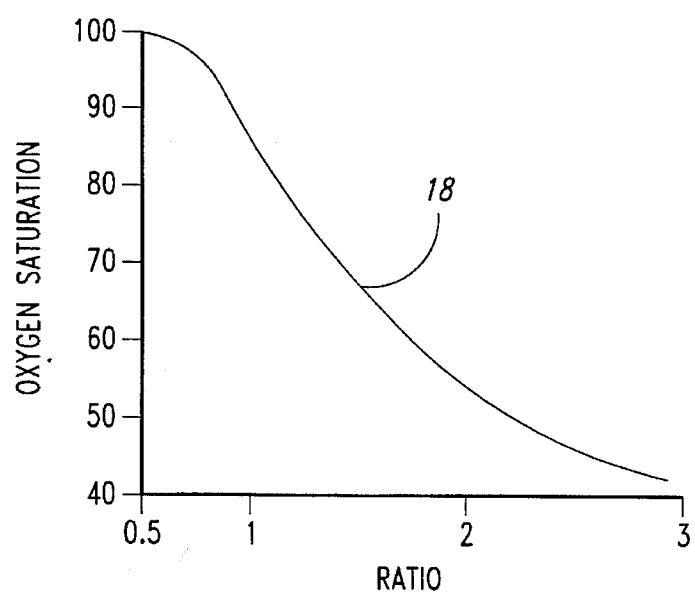
FIG. 2 is a typical oxygen saturation curve employed by the system of FIG. 1 to determine blood oxygen saturation.

As seen in equations (15) and (16), the ratio constants $\alpha$ and $\beta$ are symmetric and thus only one independent variable, either $\alpha$ or $\beta$, need be determined. The following description provides an example of the determination of the values of the ratio constants α and β. As discussed above, the ratio constant β is related to oxygen saturation in the venous system. While a curve similar to that of FIG. 2 has not been developed to indicate the oxygen saturation for the venous system, it is known that the ratio constant β can provide some measure of oxygen saturation in the venous system. For purposes of the present invention, it is assumed that oxygen consumption in the tissue is constant over the short duration of the measurement process.

Figure 7A:
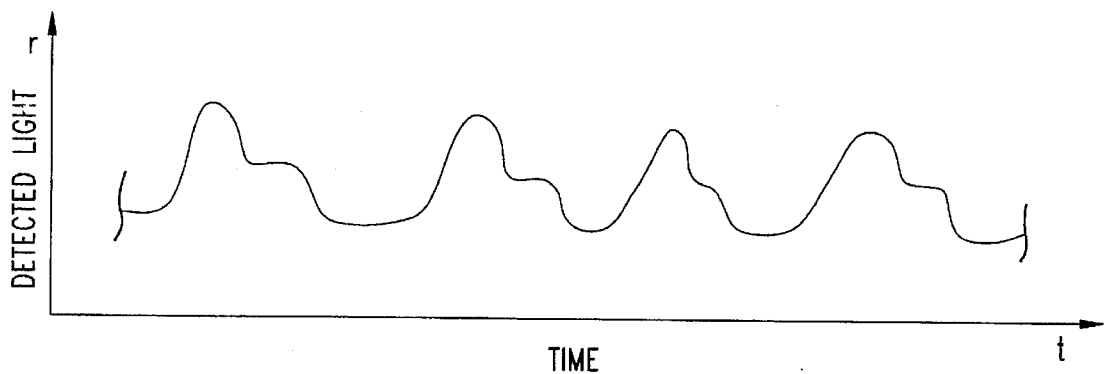
FIG. 7A illustrates a typical waveform analyzed by the system of FIG. 6.
Figure 7B:
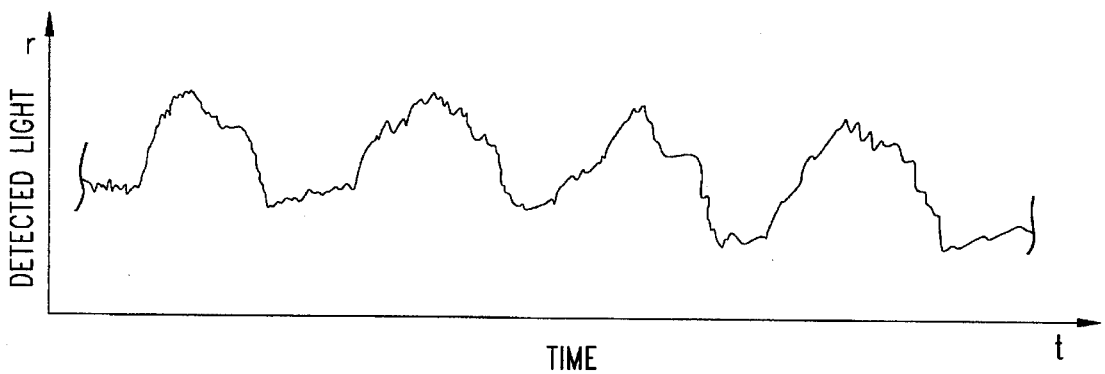
FIG. 7B illustrates another typical waveform analyzed by the system of FIG. 6.
Figure 7C:
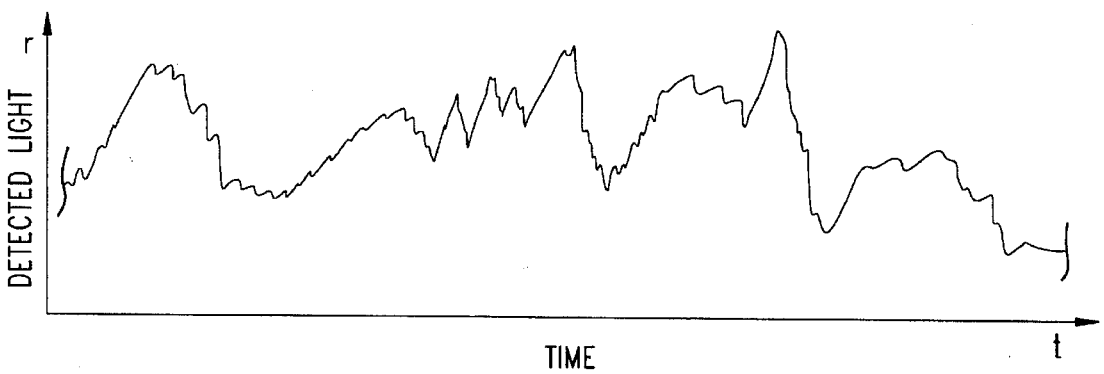
FIG. 7C illustrates another typical waveform analyzed by the system of FIG. 6.

If the detected signals have no noise (i.e., the detected signal is entirely r*(t)), the pulsatile waveform measured in equations (3) and (4) may resemble the waveform illustrated in the example of FIG. 7A. If the detected signals have a small amount of noise (e.g., r*(t)+n(t)), the pulsatile waveform measured in equations (3) and (4) may resemble the waveform illustrated in the example of FIG. 7B. If the detected signals contain only noise (e.g., n(t)), the pulsatile waveform measured in equations (3) and (4) may resemble the waveform illustrated in the example of FIG. 7C. It should be noted that the waveform of FIG. 7B is more complex than that of FIG. 7A because the noise in FIG. 7B tends to add complexity to the overall waveform relative to a normal $S_PO_2$ waveform. Similarly, the waveform of FIG. 7C is more complex than that of FIG. 7B due to the significant increase in noise in FIG. 7C.

The concept of waveform complexity can be quantitatively described by a mathematical entity called fractal dimension. In general, a more complex waveform would produce a larger fractal dimension value. This observation can be expressed mathematically by the following equation:

$$FD(r^*(t)) < FD(n(t)) \quad (17)$$

where FD denotes the "fractal dimension." Euclidean geometry has long defined objects in space using integer dimensions, such as a one dimensional line, a two dimensional plane, and a three dimensional cube. Mathematicians have recently developed the concept of real numbers for dimensions rather than the more limited Euclidean concept of integer dimensions. For example, a mathematical equation plotted on the surface of a piece of paper may not occupy the entire two dimensional plane defined by the surface of the paper. The mathematical equation may, therefore, be considered to occupy a fraction of the two dimensional plane, such as 1.3. The term fractal dimension refers to the portion of the Euclidean dimensional space occupied by a particular object. While it is simple to define the location in space of a well-defined mathematical equation, many events in nature have randomistic behavior that is not so easily defined. Fractal dimension analysis is particularly useful in such situations because an event can be characterized by its fractal dimension. Many different formulae have subsequently been developed to describe fractal dimensions for different applications, such as geological coastline analysis, flower pattern analysis, and the like. The present invention provides analysis techniques based on the complexity of measured signals. One convenient technique used to determine the complexity of the measured signals is a fractal dimension associated with the measured signals. Thus, fractal dimensions provide a quantitative indication of the complexity of the measured signals. The present invention applies the fundamental concepts of fractal analysis to physiologic waveforms. Thus, equation (17) states that the fractal dimension FD of the true signal r*(t) is less than or equal to the fractal dimension FD of the noise signal n(t). The present invention uses fractal analysis to determine the complexity of waveforms based on the premise that the true waveform with no noise will have the least complexity. Thus, the fractal dimension FD is a type of control signal that can be used to enhance the desired physiological signal.

Fractal dimensions are well known and need not be discussed in greater detail herein. The study of fractal dimensions is discussed in *The Fractal Geometry of Nature*, by B. Mandelbrot, Freeman Press, New York, 1983. The study of fractal analysis in physiologic waveforms is described in *Fractals and the Analysis of Waveforms*, by M. J. Katz, Computers In Biology and Medicine, Vol. 18(3), pp. 145–56, 1988. In his journal article, Katz describes physiologic waveforms as a special case of Mandelbrot's analysis because of the time dependency of the waveforms. The equations used herein are derived from Katz's article. However, those skilled in that art will recognize that any formula that can be used to derive the fractal value can be used with the present invention.

Based on equations (9)–(12) and (15)–(16), it is possible to define a family of functions using the following:

$$S(t,\theta) = \frac{(R(t) - \theta r(t)) * \left( \int_t R(t)r(t) - \theta \int_t r^2(t) \right)}{\int_t (R(t) - \theta r(t))^2} \quad (18)$$

where θ is a variable representing the range of possible values for the constants α and β. Equation (18) gives a time varying signal function for every value of θ. If one assumes that R(t) and r(t) are normalized AC signals, it is possible to restrict the value of the variable θ to the range from 0.3 to 3.0 and show that equation (18) contains all possible signal solutions. For the special cases in which the variable θ is equal to α or β, equation (18) simplifies to the following equations:

$$S(t,\theta) = n(t) \quad \theta = \alpha \quad (19)$$

$$S(t,\theta) = r^*(t) \quad \theta = \beta \quad (20)$$

The following formula, adapted from Fractals and the Analysis of Waveforms, relates the signal solutions of equation (18) to the fractal dimensions of equation (17):

$$FDs(\theta) \equiv FD(S(t,\theta)) = \frac{\log \left\{ \sum_i \sqrt{S^2(i+1,\theta) - S^2(i,\theta)} \right\}}{\log \left\{ \max_i \{ \sqrt{S^2(i,\theta) - S^2(0,\theta)} \} \right\}} \quad (21)$$

where the set of signal functions $S(t,\theta)$ in the θ range from 0.3 to 3.0 have been defined in equation (18). Based on equations (17) and (19)–(20), an important property of the fractal dimension is given by the following:

$$FDs(\theta) \equiv FD(n(t)) = \text{maximum}, \theta = \alpha \quad (22)$$

$$FDs(\theta) \equiv FD(r^*(t)) = \text{minimum}, \theta = \beta \quad (23)$$

where θ is defined over the range from 0.3 to 3.0.

It should be noted that the above discussion relates to the measurement of the true intensity of light transmitted from the IR light source 8. However, those skilled in the art can readily recognize that the same principles apply to the measurement of the true intensity of light transmitted from the Red light source 6. The fractal dimension property allows us to find the exact value of α and β, therefore derive the $S_PO_2$ value and noise free signals r*(t), R*(t) based on equations (9) and (10).

There are numerous conventional techniques for locating the maximum and minimum values for the fractal dimension function FDs(θ). For example, it is possible to use a "divide and conquer" technique where the range of 0.3 to 3.0 is subdivided into two substantially equal intervals and the slope is determined for the end points of each subdivided interval. If the slopes at the beginning and end points of the first interval have opposite signs (i.e., positive slope and negative slope), there must be a peak (i.e., maximum) or a valley (i.e., minimum) within the first interval. Therefore, the second interval can be discarded. The first interval is further subdivided into two smaller intervals and the slope detection process repeated until the maximum or minimum is determined.

If the slopes of the beginning and end points of the first interval have the same sign and the slopes of the beginning and end points of the second interval have opposite signs, the first interval is discarded and the divide and conquer process is repeated on the second interval. The location of the maximum and/or minimum can be determined to any degree of accuracy by selecting the minimum size for the subdivided interval. The divide and conquer technique is well known and need not be described in greater detail. There are other well-known techniques for detecting the maximum and minimum values of the fractal dimension function FDs(θ). The present invention is not limited by the particular technique used to locate the maximum and minimum values. Thus, the fractal analyzer 102 determines the values for $\alpha$ and $\beta$ based on the fractal complexity of the measured signals R(t) and r(t).

The values for the $(\alpha, \beta)$ pairs may be accumulated for a predetermined time and subjected to further statistical analysis by the statistical analyzer 104 (see FIG. 6) to select the best value for $\alpha$. For example, the mean value of $\alpha$ can be determined over a predetermined period of time and used as the best value for $\alpha$. Other forms of statistical analysis known to those of ordinary skill in the art can also be applied to select the best value for $\alpha$. The best value for $\alpha$ is then used as the index to the look-up table 14 (see FIG. 6) to determine the arterial oxygen saturation $S_PO_2$ for the patient. A peak $S_PO_2$ value can also be determined over time using the $S_PO_2$ peak detector 108 (see FIG. 6).

Figure 8:
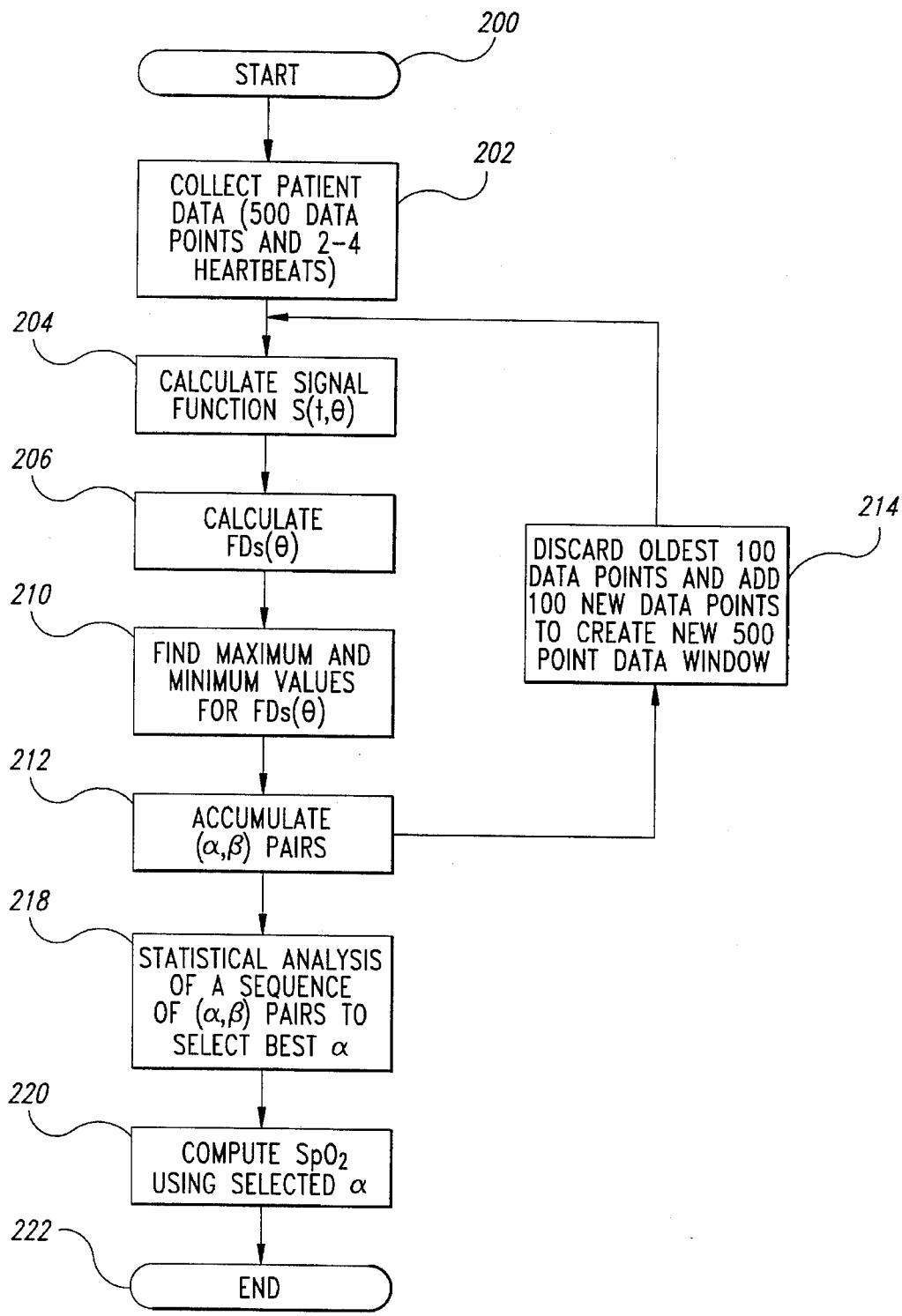
FIG. 8 is a flowchart illustrating the operation of the system of FIG. 6.

The operation of the system 100 is illustrated in the flow chart of FIG. 8 where, at the start 200, the sensor 2 has been coupled to the patient. In step 202, the system 100 collects patient data. In the presently preferred embodiment, the system 100 collects 500 data points in a data window, which includes 2–4 heartbeats. If there are less than 2 heartbeats in the data window, there may be insufficient data to properly analyze the signals. Conversely, having a large data window that includes more than 4 heartbeats generally does not provide additional information, and the computational complexity increases significantly as the size of the data window is extended. Therefore, a data window of 500 data points typically includes the 2–4 heartbeats.

In step 204, the fractal analyzer 102 (see FIG. 6) calculates the set of signal functions S(t,θ) for the collected data. In step 206, the fractal analyzer 102 calculates the fractal dimension functions FDs(θ) over the range of θ from 0.3 to 3.0. In step 210, the fractal analyzer 102 finds the maximum and minimum values for the fractal dimension functions. In step 212, the statistical analyzer 104 (see FIG. 6) accumulates the $(\alpha, \beta)$ pairs.

In step 214, the system 100 discards the oldest 100 data points and adds 100 new data points to create a new 500 point data window. The system then returns to step 204 to calculate new signal functions S(t,θ) for the new 500 point data window. Thus, the system 100 uses a sliding data window to determine the arterial oxygen saturation. While the system 100 is collecting new data points in step 214 and analyzing the new data window in steps 204–212, the statistical analyzer 104 is performing a statistical analysis of the accumulated $(\alpha, \beta)$ pairs in step 218. The statistical analyzer selects the best $\alpha$ in step 218. In step 220, the system 100 computes the $S_PO_2$ using the selected $\alpha$. As previously discussed, the selected $\alpha$ is used as an index to the look-up table 14 (see FIG. 6) to determine the $S_PO_2$ for the patient. The system ends the analysis in step 222.

The fractal analysis techniques described above provide a reliable system and method for the determination of blood oxygen saturation even in the presence of significant amounts of noise. However, certain assumptions that have been made are not correct under all real life circumstances. For example, the assumption that the true signal and the noise signal are uncorrelated is not always true. However, based on extensive analysis using both simulated data and real patient measurement data, it is possible to categorize the measured signals into one of the following five categories: (1) some motion; (2) significant motion; (3) equal motion and signal; (4) no motion; and (5) no signal. The operation of the system 100 for each of the categories is described below.

Figure 9:
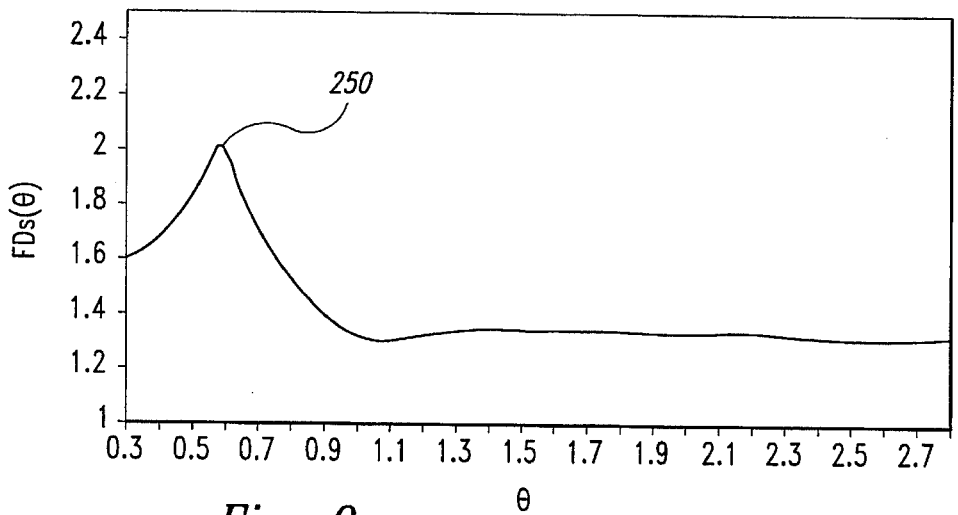
FIG. 9 illustrates a complexity distribution curve generated by the system of FIG. 6 in the presence of small amounts of noise.

The most common case is category (1) where the signal is mixed with some small amount of motion artifact. The fractal dimension function FDs(θ) has a maximum 250 at the point where θ is equal to the value of $\alpha$, which is equal to approximately 0.55 in the example illustrated in the graph of FIG. 9.

Figure 10:
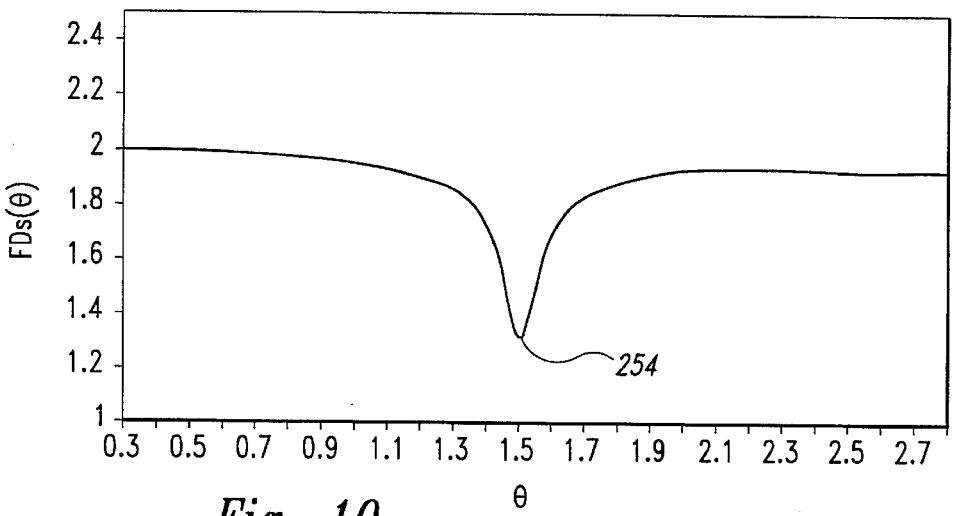
FIG. 10 illustrates a complexity distribution curve generated by the system of FIG. 6 in the presence of a significant amount of noise.

In the situation of category (2) where there is a significant amount of noise, the system receives very little arterial signal. The fractal dimension function FDs(θ), illustrated in the graph of FIG. 10, has a relatively high value except at the point where θ is equal to the value of $\beta$ where the desired arterial signal is found. The graph of FIG. 10 has a minimum 254 at the point where θ is equal to the value of $\beta$, which is equal to approximately 1.5 in the example of FIG. 10.

Figure 11:
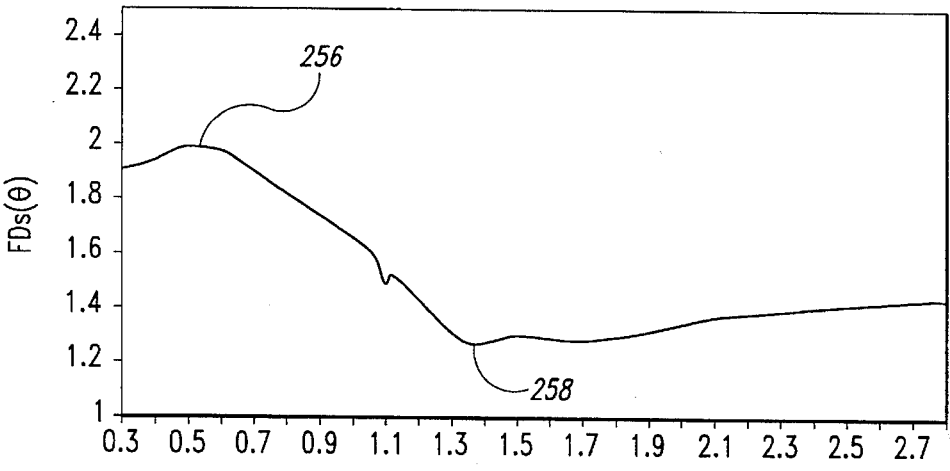
FIG. 11 illustrates a complexity distribution curve generated by the system of FIG. 6 in the presence of substantially equal amounts of signal and noise.

In certain circumstances, the artifact noise signal will be approximately equal in strength to the desired arterial signal, which corresponds to category (3) above. Under these conditions, the data window tends to include distinguishable maximum and minimum values for the fractal dimension function FDs(θ), as illustrated in the graph of FIG. 11. The fractal dimension function FDs(θ) has a maximum 256 at the point where θ is equal to the value of $\alpha$, which is equal to approximately 0.5 in the example of FIG. 11, and a minimum 258 at the point where θ is equal to the value of $\beta$, which is equal to approximately 1.35 in the example of FIG. 11. Although the curve of FIG. 11 does not contain sharp peaks for the maximum and minimum values, it is nonetheless possible to determine the maximum and minimum values for the fractal dimension function FDs(θ).

Figure 12:
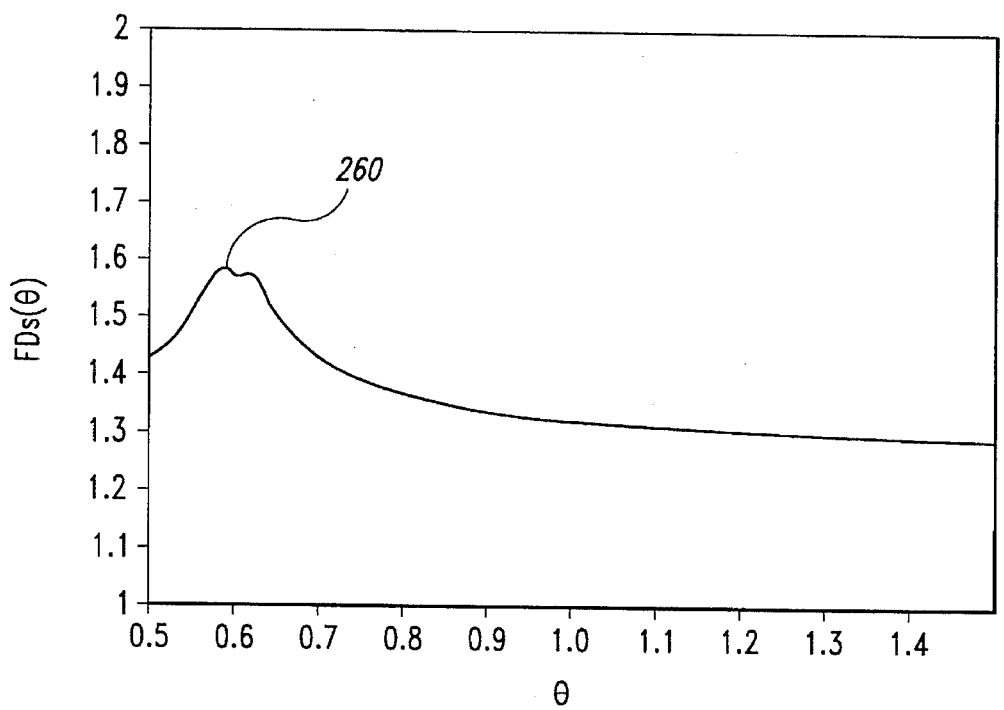
FIG. 12 illustrates a complexity distribution curve generated by the system of FIG. 6 with substantially no motion artifact.

The previous description has assumed that it was always possible to derive values for $\alpha$ and $\beta$. However, in certain cases, values for one or both of the ratio constants $\alpha$ and $\beta$ may not exist. For example, in a measurement cycle in which the subject is completely still, there is no motion artifact. This corresponds to category (4) above. In this relatively unusual case, equations (9)–(13) and (16) are no longer valid because there is no noise signal. However, experiments indicate that the fractal dimension function FDs(θ) still has a maximum 260, as illustrated in the graph of FIG. 12. The fractal dimension function FDs(θ) has the maximum 260 at the point where θ is equal to the value of $\alpha$, which is equal to approximately 0.6 in the example of FIG. 12. This may indicate that category (4) may not actually exist and that there is always some motion artifact (i.e., category 1) that may be due to the flow of blood in the venous system.

Figure 13:
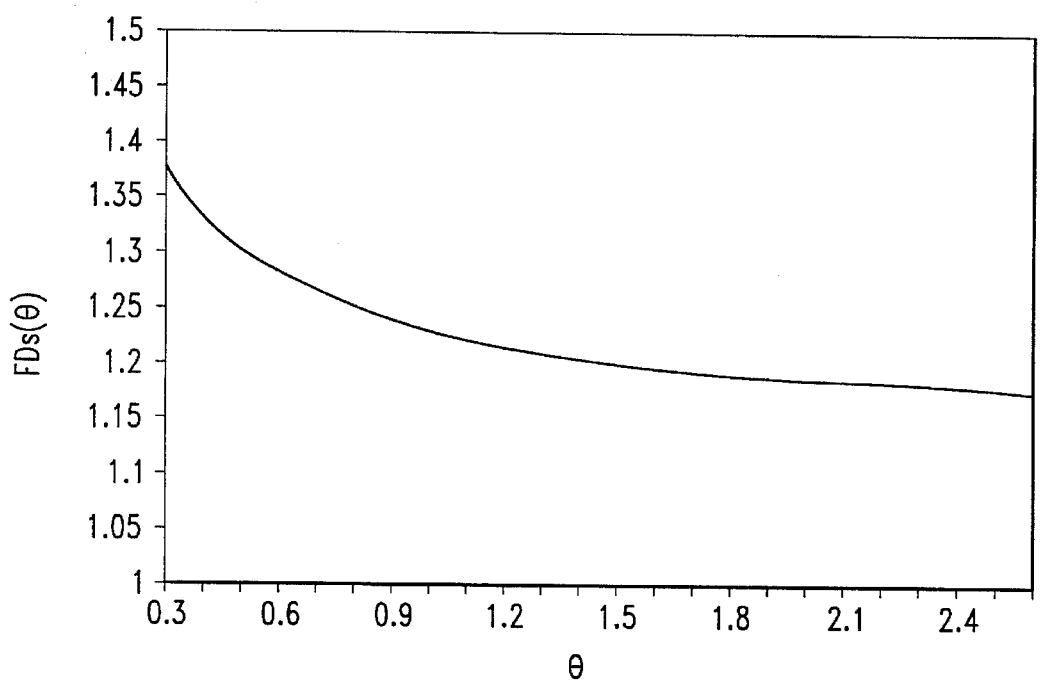
FIG. 13 illustrates a complexity distribution curve generated by the system of FIG. 6 with no signal.

Another example of a case in which $\alpha$ and/or $\beta$ values may not exist is a measurement cycle in which there is no arterial signal, category (5) above. This occurs only in the special case in which the sensor 2 (see FIG. 6) is off of the patient or is unplugged from the rest of the system 100. This is another unusual case in which equations (9)–(13) and (16) are no longer valid because there is no arterial signal. As illustrated in FIG. 13, the fractal dimension function $FD_s(\theta)$ behaves differently from that of the other four categories discussed above. The fractal dimension function $FD_s(\theta)$ in category (5) produces a smooth curve without any maxima or minima. This condition does not produce blood oxygen data, but can be used to detect a "probe off patient" condition and provide an indication to the user. Thus, the analysis demonstrates that the fractal dimension method may not produce $\alpha$, $\beta$ values for every data set, depending on the actual signal content.

Figure 3:
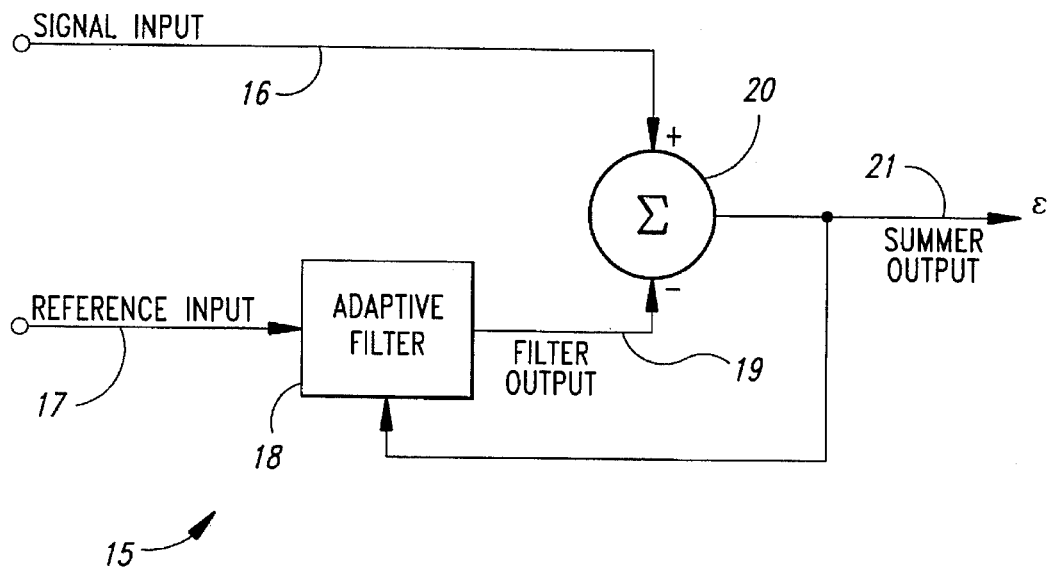
FIG. 3 is a functional block diagram of a conventional adaptive signal processor.

The fractal analysis of pulse oximetry signals can also be used with the adaptive signal processor 15 (see FIG. 3). Equation (12) is used as the reference signal 17 to represent the noise $n(t)$ and is varied over the known physiological range for $\alpha$. The measured signal $r(t)$, which is the sum of the true intensity $r^*(t)$ and the noise signal $n(t)$, is applied to the signal input 16 of the adaptive signal processor 15. The summer output 19 is used as a control signal to adjust the adaptive filter 18. The fractal analyzer 102 (see FIG. 6) analyzes the summer output 21 of the adaptive signal processor 15 in the manner previously described to determine maximum and minimum fractal values corresponding to $\alpha$ and $\beta$, respectively. It is known that the adaptive signal processor 15 can be configured in different ways other than the example illustrated in FIG. 3. However, the principles of the present invention can be readily applied to other configurations of the adaptive signal processor 15. The output of the fractal analyzer 102 (see FIG. 6) is used to select the proper reference signal 17.

It should be noted that the principles of the present invention may be extended beyond the measurement of blood oxygen saturation. For example, a third light source (not shown) may be added to produce a third wavelength in the sensor 2 (see FIG. 5). Three ratios of light intensities (e.g., ratio of light source one to light source two, ratio of light source one to light source three, and ratio of light source two to light source three) can be derived from the light detector 10. The three ratios can be independently used to derive both the arterial oxygen saturation and the arterial carboxyhemoglobin saturation period. The present invention is also not limited solely to the use of optical sensors. Electrical sensors may derive physiological signals that can be processed according to the principles of the present invention. For example, electrical sensors can be used to derive a noise-free ECG signal. The electrical sensors each derive an ECG signal and the ratios of the ECG signals may be used to derive a noise-free version of the true ECG signal. The fractal analysis of the present invention can derive noise-free physiological signals in a variety of conditions.

The present invention is described herein using the example of pulse oximetry. In this situation, the minimum fractal dimension FD corresponds to the value of $\alpha$. However, with other physiological measurements, it may be desirable to select a signal having the maximum value for the fractal dimension FD. For example, an ECG signal is often contaminated by interference from a low frequency respiratory signal. Under these circumstances, the minimum fractal dimension FD may correspond to the respiratory signal rather than the desired ECG signal. The maximum fractal dimension FD may correspond to the desired ECG signal.

In operation, many of the components described above may be incorporated into a digital signal processor and/or a digital computer. The programming details of the digital signal processor and computer are well known to those of ordinary skill in the art and need not be discussed herein.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the enhancement of physiological signals for the measurement of blood oxygen in a subject, the system comprising:

first and second light sources to direct light toward the subject, said first and second light sources producing light of first and second wavelengths, respectively;

a light detector positioned to detect first and second light signals after interacting with the subject and to generate signals indicative of an intensity of said first and second detected light signals, said first detected signal having a first portion arising from light transmitted from said first source and a second portion arising from a first interference source, said second detected signal having a first portion arising from light transmitted from said second source and a second portion arising from a second interference source;

a storage location containing a mathematical relationship of said first and second portions of said first and second detected signals and a first ratio of said first portion of said first detected signal to said first portion of said second detected signal;

an analyzer coupled to said storage location to determine a plurality of complexity values for said mathematical relationship over a predetermined range of said first ratio; and a calculator to determine a selected value for said first ratio based on said complexity values.

2. The system of claim 1 wherein said analyzer uses fractal dimension analysis to determine said complexity values.

3. The system of claim 1 wherein said calculator determines said selected first ratio value by finding a maximum value for said plurality of said complexity values.

4. The system of claim 1 wherein said storage location contains a second ratio of said second portion of said first detected signal to said second portion of said second detected signal and having a range corresponding to said predetermined range, said calculator determining a selected value for said second ratio by finding a minimum value for said plurality of said complexity values.

5. The system of claim 1 wherein said first ratio is indicative of blood oxygen saturation in the subject, the system further including a look-up table containing data relating said first ratio to said blood oxygen saturation.

6. The system of claim 1 wherein said mathematical relationship has the following form:

$$S(t,\theta) = \frac{(R(t) - \theta r(t)) * \left( \int_t R(t)r(t) - \theta \int_t r^2(t) \right)}{\int_t (R(t) - \theta r(t))^2}$$

where R(t) is said first detected signal, r(t) is said second detected signal, and θ is a variable defined over a predetermined range.

7. The system of claim 6 wherein said predetermined range for said variable θ is substantially 0.3 to 3.0, said fractal analyzer analyzing said mathematical relationship over said predetermined range for said variable θ.

8. The system of claim 1, further including a statistical analyzer coupled to said calculator to receive a plurality of values for said first ratio over a predetermined period of time, said statistical analyzer analyzing said plurality of selected values for said first ratio and determining a statistical value for said first ratio.

9. The system of claim 8 wherein said statistical value for said first ratio is a mean value for said plurality of selected values for said first ratio.

10. The system of claim 1, further including an adaptive signal processor having a signal input, a reference input, an adaptive filter coupled to said reference input and generating a filter output, a summer coupled to said signal input and said filter output to generate a summer output, said signal input receiving said first detected signal and said reference input receiving a signal derived from said mathematical relationship defined over said predetermined range, said analyzer analyzing said summer output to determine said complexity value of said summer output.

11. A system for the enhancement of physiological signals representative of a physiological phenomenon in a subject, the system comprising:

a sensor positioned in proximity with the subject to detect physiological signals and to generate signals indicative of said detected physiological signals, said detected signals having a first portion arising from the physiological phenomenon and a second portion arising frown an interference source;

an analyzer to analyze and determine a complexity value for said generated signals, said complexity value being indicative of a complexity of said generated signals; and a processor, responsive to said complexity value, to generate a processed signal.

12. The system of claim 11 wherein said analyzer is a fractal analyzer determining a fractal value for said complexity value.

13. The system of claim 11 wherein said analyzer determines said complexity values over a predetermined range of possible complexity values and said processor selects a maximum value for said range of possible complexity values.

14. The system of claim 11 wherein said analyzer determines said complexity values over a predetermined range of possible complexity values and said processor selects a minimum value for said range of possible complexity values.

15. The system of claim 11 wherein said complexity value is valid over a predetermined range, and said analyzer selects a value for said complexity value in said predetermined range.

16. The system of claim 11 wherein said processor is an adaptive signal processor having a signal input, a reference input, an adaptive filter coupled to said reference input and generating a filter output, a summer coupled to said signal input and said filter output to generate a summer output, said signal input receiving said detected signals and said reference input receiving a signal derived from a mathematical relationship of said first and second portions of said detected signals, said analyzer analyzing said summer output to determine said complexity value of said summer output.

17. The system of claim 16 wherein said processed signal is said filter output.

18. The system of claim 11 wherein said detected signals are first and second light signals transmitted from first and second light sources having first and second wavelengths, respectively, each of said detected signals having said first and second portions, the system further including a light detector positioned to detect first and second light signals after interacting with the subject and to generate signals indicative of an intensity of said first and second detected light signals, a storage location containing a mathematical relationship of said first and second portions of said first and second detected signals and a first ratio of said first portion of said first detected signal to said first portion of said second detected signal, said analyzer being coupled to said storage location to determine a plurality of complexity values for said mathematical relationship over a predetermined range of said first ratio, said first ratio being based on said complexity values.

19. The system of claim 18 wherein said analyzer determines said first ratio value by finding a maximum value for said plurality of said complexity values.

20. The system of claim 18 wherein said storage location contains a second ratio of said second portion of said first detected signal to said second portion of said second detected signal and having a range corresponding to said predetermined range, said analyzer determining a selected value for said second ratio by finding a minimum value for said plurality of said complexity values.

21. The system of claim 18 wherein said first ratio is indicative of blood oxygen saturation in the subject, the system further including a look-up table containing data relating said first ratio to said blood oxygen saturation.

22. A method for the enhancement of physiological signals for the measurement of blood oxygen in a subject, the method comprising the steps of:

producing light of first and second wavelengths;

directing light of said first and second wavelengths toward the subject;

detecting first and second light signals after interacting with the subject and generating signals indicative of an intensity of said first and second detected light signals, said first detected signal having a first portion arising from light transmitted with said first wavelength and a second portion arising from a first interference source, said second detected signal having a first portion arising from light transmitted with said second wavelength and a second portion arising from a second interference source;

analyzing said first and second detected signals using a mathematical relationship of said first and second portions of said first and second detected signals and a first ratio of said first portion of said first detected signal to said first portion of said second detected signal to determine a plurality of complexity values for said mathematical relationship over a predetermined range of said first ratio; and determining a selected value for said first ratio based on said complexity values.

23. The method of claim 22 wherein said step of analyzing uses fractal dimension analysis to determine said complexity values.

24. The method of claim 22 wherein said step of determining said selected value selects a maximum value for said plurality of said complexity values.

25. The method of claim 22 wherein said mathematical relationship contains a second ratio of said second portion of said first detected signal to said second portion of said second detected signal, said second ratio having a range corresponding to said predetermined range, said step of determining also determining a selected value for said second ratio by finding a minimum value for said plurality of said complexity values.

26. A method for the enhancement of physiological measurements in a subject, the method comprising the steps of:

using a plurality of light sources, each producing light of a different predetermined wavelength;

directing light of said predetermined wavelengths toward the subject;

detecting a plurality of light signals after interacting with the subject and generating signals indicative of an intensity of said plurality of detected light signals, each of said detected signals having a first portion arising from light transmitted with one of said predetermined wavelength and a second portion arising from an interference source;

analyzing said plurality of detected signals using a mathematical relationship of said first and second portions of said plurality of detected signals and a first ratio of said first portion of a first of said plurality of detected signals to said first portion of a second of said plurality of detected signals to determine a plurality of complexity values for said mathematical relationship over a predetermined range of said first ratio; and determining a selected value for said first ratio based on said complexity values.

27. The method of claim 26 wherein said step of analyzing uses fractal dimension analysis to determine said complexity values.

28. The method of claim 26, further including the steps of analyzing said plurality of detected signals using said mathematical relationship and a second ratio of said first portion of said first of said plurality of detected signals to said first portion of a third of said plurality of detected signals to determine a plurality of complexity values for said mathematical relationship over a predetermined range of said second ratio, and determining a selected value for said second ratio based on said complexity values.

29. A method for the enhancement of physiological signals representative of a physiological phenomenon in a subject, the method comprising the steps of:

positioning a sensor in proximity with the subject to detect physiological signals and to generate signals indicative of said detected physiological signals, said detected signals having a first portion arising from the physiological phenomenon and a second portion arising from an interference source;

analyzing said generated signals to determine a complexity value for said generated signals, said complexity value being indicative of a complexity of said generated signals; and processing said generated signals using said complexity value to generate processed signals.

30. The method of claim 29 wherein said step of analyzing uses fractal dimension analysis to determine said complexity values.

* * * * *

UNITED STATES PATENT AND TRADEMARK OFFICE
CERTIFICATE OF CORRECTION

PATENT NO.    : 5,588,427
DATED         : December 31, 1996
INVENTOR(S)   : Jonathan Tien It is certified that error appears in the above identified patent and that said Letters Patent is hereby corrected as shown below:

In column 15, claim 11, line 42, please delete "frown" and insert therefor --from--.

Signed and Sealed this

Twelfth Day of August, 1997

Attest:

BRUCE LEHMAN

*Attesting Officer*    *Commissioner of Patents and Trademarks*